United States Patent [19]

Marston

[11] 4,135,269
[45] Jan. 23, 1979

[54] MOP STERILIZER AND DRYER

[76] Inventor: Laurel L. Marston, 926 New York Ave., Brooklyn, N.Y. 11203

[21] Appl. No.: 852,827

[22] Filed: Nov. 18, 1977

[51] Int. Cl.² .................... A61L 3/00; A47L 13/60
[52] U.S. Cl. .......................................... 15/4; 15/262;
15/264; 422/24
[58] Field of Search .............. 15/4, 262, 264, DIG. 9;
21/54 R, DIG. 2

[56] References Cited
U.S. PATENT DOCUMENTS

| 1,453,450 | 5/1923 | Dilas | 15/264 UX |
| 1,767,840 | 6/1930 | Finnell | 15/264 |
| 3,058,134 | 10/1962 | Wozniak-Rennek | 15/4 X |
| 3,820,251 | 6/1974 | Abernathy | 21/54 R X |
| 3,955,922 | 5/1976 | Moulthrop | 21/102 R |

*Primary Examiner*—Daniel Blum

*Attorney, Agent, or Firm*—Robert D. Farkas

[57] ABSTRACT

A mop sterilizer and dryer utilizes a wheel-supported cart having a pair of drainable compartments therein. One of the drainable compartments has an open-mouth portion carrying a pair of squeeze rolls adapted to squeeze the fabric cord-like elements of a mop therebetween. Water captured within such compartment is strained and carried by the cart. The other compartment is totally lined with a reflective material adapted to reflect ultraviolet rays generated by ultraviolet lamp sources disposed within the other compartment. At least one opening is provided in the other compartment in which the cord or strand elements of a mop is disposed during a drying and sterilizing operation, having its handle secured in an upright position by a bracket having a notch at the uppermost free end thereof.

9 Claims, 3 Drawing Figures

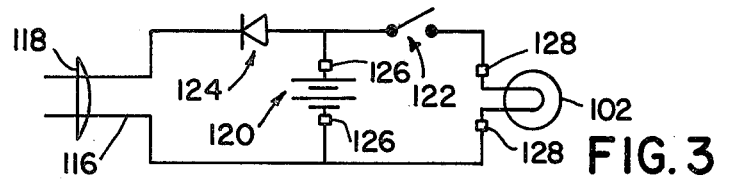
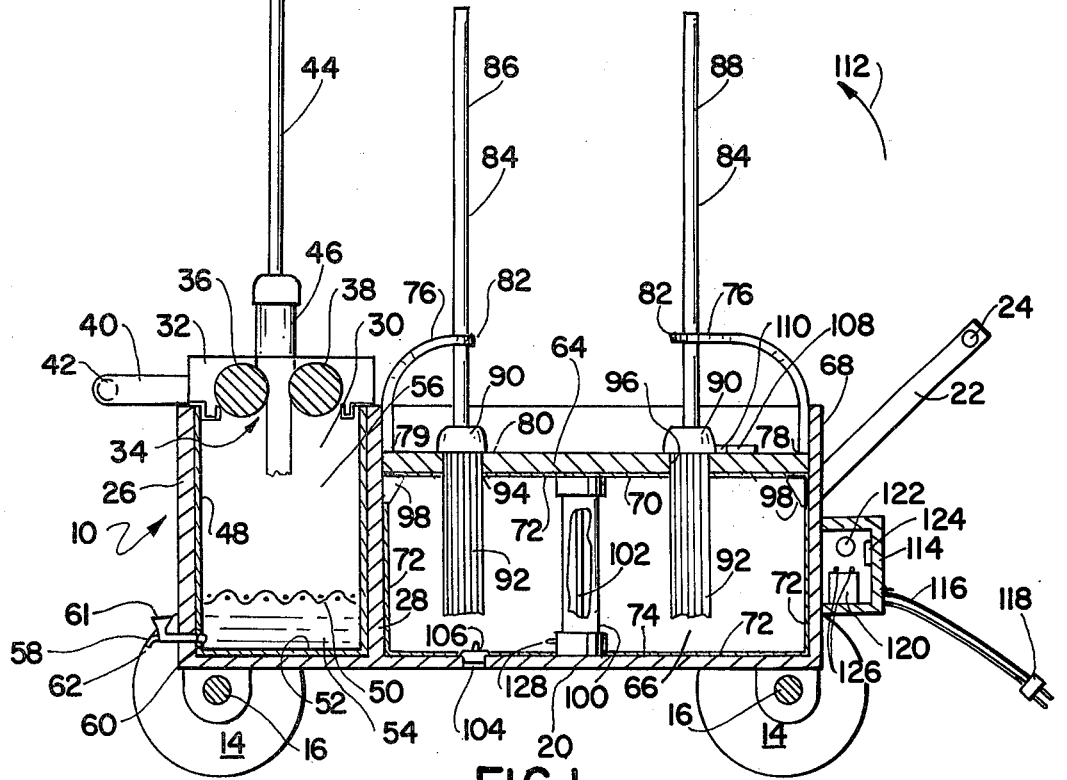
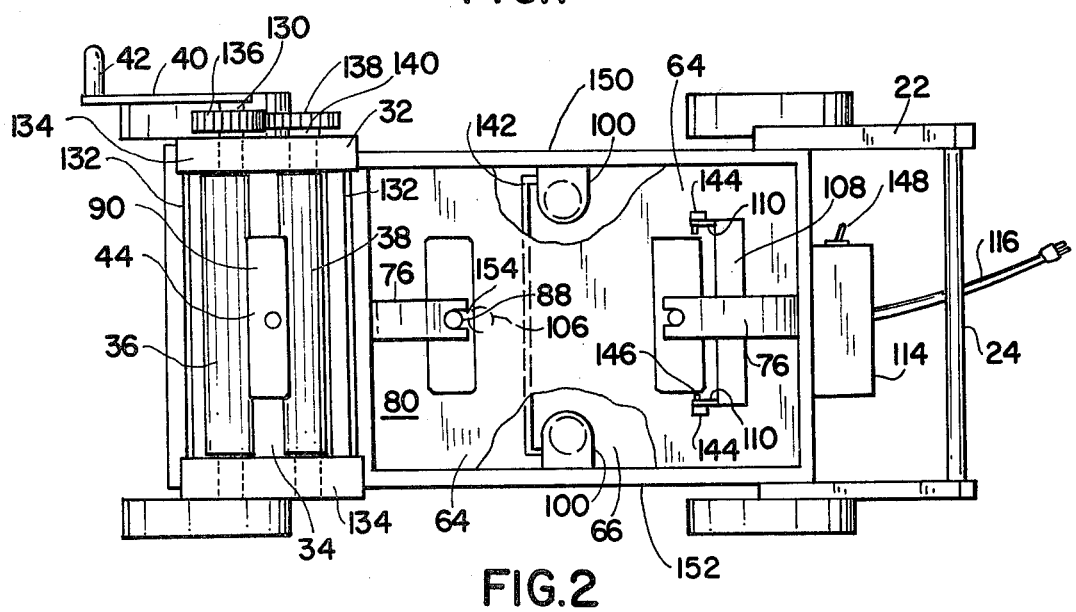

MOP STERILIZER AND DRYER

BACKGROUND OF THE INVENTION

1. The Field of the Invention

This invention relates to sterilizing and drying apparatus for cleaning articles and more particularly to that class adapted to be carried about by a cart having separate compartments for each functional purpose.

2. Description of the Prior Art

The prior art abounds with sterilizers of various types. U.S. Pat. No. 3,955,922 issued on May 11, 1976 to L. E. Moulthrop teaches a sterilizer for bathroom articles for toothbrushes, dentures, combs, hairbrushes and the like having a box including a hinged lid with a mirror on the underside of the lid. A removable foraminous tray is supported above the bottom of the box and the items to be sterilized are placed thereon. A container of volatile disinfectant is disposed beneath the tray, as are also a fan and a plurality of ultraviolet lights. The mirror serves both as a vanity mirror and as a reflector to augment the action of the ultraviolet lights. The lights and the fan are in series so that the fan motor ballasts the lights. The Moulthrop device, though utilizing ultraviolet reflectors within the box relies upon the articles being sterilized therein resting upon a tray, thus precluding such light from contacting the surface of such article in touching engagement with the tray.

U.S. Pat. No. 3,683,638 issued on Aug. 15, 1972 to G. S. Devon discloses a drying and sterilizing cabinet especially suited for use in hospitals. The cabinet is sealed and has a dehumidifying chamber at its rear through which filtered air flows. Bacteria are killed by an arrangement of ultraviolet rays inside the cabinet. The cabinet is provided with a plurality of foraminous shelves disposed in a vertical array, one above the other, upon which the articles to be sterilized rest. This apparatus suffers substantially the same deficiency as the apparatus here and above described by Moulthrop.

U.S. Pat. No. 3,820,251 issued June 28, 1974 to H. O. Abernathy discloses a toothbrush drying device having an interior compartment in which heated air is circulated and in which a plurality of toothbrushes are disposed having their bristles free of engagement of a supporting apparatus, supporting the toothbrush. The Abernathy apparatus, though effectively drying the bristles of the toothbrush, both by heat and by exposure to ultraviolet, serving a sterilizing function, is totally unsuitable for use with articles having a substantial amount of moisture trapped therewithin and especially with articles whose size and shape do not permit portions of the article to extend outwardly from the compartment portion thereof.

SUMMARY OF THE INVENTION

A primary object of the present invention is to provide a wheeled cart suitable for drying and sterilizing mop cords.

Another object of the present invention is to provide a cart-carried compartment suitable for wringing out the cords of a mop.

Still another object of the present invention is to provide a cord sterilizing compartment carried by a cart.

Yet another object of the present invention is to provide an ultraviolet radiating source which has the rays emanating therefrom reflectively directed from the walls of the compartment carrying the ultraviolet source.

A further object of the present invention is to provide a mop-supporting bracket, adapted to maintain a mop handle in a vertical direction when its corded end is disposed irradiated by ultraviolet means.

Another object of the present invention is to provide a coverable opening of the ultraviolet contained compartment so as to insure the ultraviolet rays do not emerge outwardly therefrom.

Still another object of the present invention is to provide drains for each of the aforementioned compartments insuring that such compartments may be effectively cleaned and emptied of accumulated moisture therein.

Yet another object of the present invention is to provide a rechargeable battery source for use operating the aforementioned ultraviolet light generator, during periods in which the cart is being transported from place to place.

A further object of the present invention is to provide an ultraviolet energizing apparatus which maintains such apparatus energized, selectively as desired, at times when the cart is in use at a temporary location and when the cart is stored at a fixed location for extended periods of time.

Heretofore, mopping operations utilized mops that had to be set aside for extended periods of time, after use, so as to enable such used mops to be wrung dry and if desired, sterilized. The facilities required for use in wringing and drying and sterilizing such used mops are often located at locations other than the locations in which the mop is to be utilized. Thus, the user was required to maintain a substantial quantity of mops so as to be able to continue to utilize mops in a continuous fashion and to allow used mops to dry in between their use periods.

The present invention recognizes these problems and by providing a battery pack operated ultraviolet source, carried on a rolling cart, also having thereon a wringing type arrangement, enables used mops to be stored on the cart, and during such storage periods to be sterilized, utilizing the ultraviolet source carried thereby. The wringing compartment is provided with a drain valve adjacent the lowermost regions thereof and below a screen-like filter adapted to trap thereon particles of dirt not disolved within the water wrung out from the mop. The ultraviolet lamp source carrying compartment is lined with a reflective material on the base and interior walls and roof portion thereof accepting openings in the roof portions through which the cord end of a mop may be inserted. A hingeable lid is provided which covers such openings when they are not utilized in having the bristle end of the mop pass there through. The battery pack is operated from a line cable which permits the line cord to provide energizing power derived from a convenient household utility voltage source to recharge the battery, as desired. At all other times, the battery may be employed in providing operating power to the ultraviolet source, provided however that an on-off operating switch, disposed in series electrical circuit with the ultraviolet source and the battery is in a closed circuited condition. A drain is provided for the compartment carrying the waterproof ultraviolet light sources so as to permit accumulated water to be drained therefrom. The wheeled cart is also provided with a handle which enables the user to propel the device from place to place in which the mop-carrying cart is adapted to be used or to be stored when recharging the battery pack. During such transporting times and during the times that the cart is located away from an outlet providing recharging or operating voltage, the battery provides the energizing power for the ultraviolet lamp.

These objects as well as other objects of the present invention, will become more readily apparent after reading the following description of the accompanying drawings.

BRIEF DESCRIPTION OF THE DRAWINGS

FIG. 1 is a side elevation cross-sectional view of the present invention.

FIG. 2 is a plan view of the apparatus shown in FIG. 1 with parts broken away.

FIG. 3 is a schematic representation of the electrical components used in the present invention.

DESCRIPTION OF THE PREFERRED EMBODIMENT

The structure and method of fabrication of the present invention is applicable to the wheeled cart having a handle extending outwardly therefrom residing in a horizontal plane for propulsion purposes. The cart carries a pair of compartments, each having open-mouth portions residing adjacent one another and disposed over the sidewalls of the compartments. One of the compartments is provided with a lid apparatus having a pair of rollers whose longitudinal axes are disposed in parallel spaced-apart relationship alongside an elongated opening therein between. One of the rollers is provided with a crank handle and a gear. The other roller is also provided with a gear meshing with the gear carried by a roller equipped with a crank. A mop, having cords, is wrung out by having the cord end of the mop, often described as the strand-like end, disposed between the rollers at a time when the crank handle is rotated such that the rollers pinch the cords and wring out moisture contained therewithin. A grate is disposed within the compartment supporting the wringing rollers, the grate located somewhat above the floor of such compartment. A valve is mounted on the exterior walls of such compartment and communicates through an opening in a liner disposed within the compartment to which the tray is secured, utilizing an O-ring preferably fabricated from rubber, so as to make a good seal between the water impervious liner and the interior walls of the compartment. Opening the valve, when desired, permits the accumulated water, stored below the surface of the straining tray to be emptied from the liner, as desired.

The other compartment is provided with a cover, removable in nature, and having its lowermost surface lined with a light-reflective material, such as a mirror, a sheet of highly polished stainless steel or the like. The sidewalls and floor of the other compartment are similarly covered by an equivalent light-reflective material. The cover is provided with at least one opening which is adapted to receive therethrough the cords of a mop when the mop handle is disposed in vertical arrangement over the uppermost layer of the cover. A bracket, preferably fabricated from a rigid material, such as steel, extends upwardly from the uppermost surface of the cover and inwardly towards the opening. The free end of the bracket is provided with a notch adapted to receive therein a portion of an upstanding mop whose cords are positioned within the opening in the cover. A drain is provided within the floor of the other compartment, utilizing a drain-hole plug, removably affixed therein, when it is desired to clean or empty accumulated water from within the other compartment. At least one ultraviolet ray generating lamp is disposed within a waterproof housing, carried within the other compartment. Energizing power is provided to the ultraviolet lamp from a battery source, also carried by the cart. The battery source is disposed within an openable housing, also carrying an operating switch and an appropriate alternating current rectifier and a switch. A line cable extends outwardly from the housing and is provided with a household utility plug at the distal end thereof. The other end of the cable is coupled to a series circuit consisting of the rectifier and terminals of the battery. Another series circuit couples the terminals of the ultraviolet lamp and the switch and the terminals of the battery together. The rectifier may provide an appropriate charging voltage for the battery, in direct current from and of the correct magnitude, as well as operating current for the lamp, when the lamp operating switch is disposed in closed-circuit condition by the user. Thus, the lamp may be energized utilizing selectively the battery and the line cable, when such line cable is provided with energizing power from a remote source. Alternatively, the battery alone may provide operating power for the ultraviolet light ray generating lamp when the operating switch is maintained in closed-circuited condition and the line cable is not operated by a remote voltage alternating current source.

Now referring to the figures, and more particularly to the embodiment illustrated in FIG. 1 showing the present invention 10 having wheels 14 journaled on axles 16 of cart-like structure 20. Bars 22 extend upwardly and outwardly from cart structure 20 and are provided with handle 24 at the end thereof. Vertical walls 26 contain compartment cavity 30 therein between. Lid or cover 32 is shown partially covering open-mouth portion 34 of compartment 30 and is provided with rollers 36 and 38 journaled to cover 32, in spaced-apart parallel relationship. Crank 40 is shown extending outwardly from cover 32 and is provided with handle 42. Mop 44 is shown having cords 46 thereof inserted between adjacent surfaces of rollers 36 and 38. Liner 48 is shown within compartment 30 having an equivalent open-mouth portion to open-mouth portion 34. Screen-like tray 50 is shown disposed above floor 52, of liner 48. Water 54 is shown accumulated above floor 52 and is drainable outwardly from the cavity 56, of liner 48, utilizing valve 58 therefor. Rubber-like O-ring 60 lines opening 62 in liner 48, so as to provide a watertight seal between the interior surface of wall 24 and the exterior vertical surface of liner 48 adjacent thereto. Operating valve handle 61, in the appropriate direction, permits water 54 to be drained outwardly from end 62 of valve 58.

Cover 64 is shown disposed over cavity 66 formed by wall 28, wall 68, and walls 150 and 152, shown in FIG. 2. Lowermost surface 70, of cover 64 is provided with a light reflective liner 72. Lining material 72 also covers floor 74, of compartment 66 and interior surfaces of the walls defining compartment 66. Brackets 76 are shown having ends 78 thereof secured to uppermost surface 80 of cover 64. Ends 82 of brackets 76 are provided with notches adapted to receive therein handles 84 of mops 86 and 88. Mop portions 90, affixed to mops 86 and 88, rest upon surface 80 and are utilized to secure cords 92 thereof to handles 84 and provide vertical support for mops 86 and 88 thereby. Openings 94 and 96 are formed in cover 64 and in portions of lining 72 carried on surface 70. Cords 92 pass through such openings and reside, in the main, in compartment 66. Brackets 98 provide vertical support for cover 64. Waterproof housings 100, each contain therewithin ultraviolet lamp source 102, and are carried within compartment 66. Opening 104 is disposed in surface 74 and in a portion of lining 72, adjacent thereto, so as to permit stopper 106 to maintain compartment 66 in a waterproof condition. It should be noted that handles 84 and 44 are substantially operated in a vertical condition when cords 46 are being wrung by rollers 36 and 38 and when handles 84 are supported by cover 64 and brackets 76. Lid 108 is carried by arms 110, and when disposed moved in the direction of arrow 112, may be utilized to cover opening 96 provided mop 88 is removed from opening 96, thereby sealing therewithin ultraviolet rays, not shown, in the interior of compartment 66. Housing 114 is shown having line cable 116 extending outwardly therefrom. The line cable is provided with a plug 118, for use with a household utility outlet, not shown. Rechargeable battery 120 is shown disposed within housing 114 and, such housing also carrying switch 122 and rectifier 124. Rectifier and terminals 126, of battery 120 and the conductors of cable 116, not shown, are all disposed in a series electrical circuit, by wires, not shown. Switch 122 and terminals 128, of lamp 102, and terminals 126 of battery 120, are all disposed in a series electrical circuit by wires, not shown.

FIG. 2 illustrates rollers 36 and 38 disposed adjacent element 90 of mop 44. Crank 40 is shown having handle 42 thereof disposed extending outwardly from shaft 130, carrying roller 36 in journaled fashion to cover 32. Rods 132 extend between end elements 134 and make up the totality of cover 32. Gear 136 is carried by shaft 130 and engages gear 138, carried by shaft 140, also carrying roller 38 in journaled fashion. Compartment 66 is shown covered by lid 64, revealing housings 100 there below, coupled together by electrical cable 142. Brackets 76 are shown provided with notches 154, in which handles 84 are carried. Lid 108 is shown supported by arms 110 which in turn are pivoted to blocks 144 fastened to the uppermost surface 80 of cover 64. Pivot rods 146 enable lid 108 to be pivotably located above opening 96, shown in FIG. 1, when desired. Housing 114 is shown having switch operating arm element 148 extending outwardly therefrom, as well as line cable 116. When it is desired to clean the interior of compartment 66, lid 64, carrying brackets 76, may be lifted upwardly, so as to expose compartment 66 and waterproof housings 100 thereby.

FIG. 3 depicts the electrical components utilized in the present invention, consisting of rectifier 124, battery 120, line cable 116 and plug 118 all in a series electrical circuit, in which terminals 126 of battery 120 are utilized. Charging voltage obtained by applying plug 118 to a convenient source of alternating current provides a charging circuit of direct current to battery 120. When switch 122 is closed, the series electrical circuit comprising lamp 102, having terminals 128 thereof in such circuit, and battery 120 and switch 122 is useful in providing energizing power to lamp 102, wherein such energizing power is derived from battery 120 alone, when plug 118 is not inserted into a source of alternating voltage, or, alternatively, when battery 120 is being simultaneously charged by the direct current passing through rectifier 124, derived from such alternating current source that might be coupled to plug 118. In the latter case, the alternating current source may simultaneously charge up battery 120 whilst providing operating energy to lamp 102, provided that switch 122 is in the closed circuited condition. When switch 122 is in the open circuited condition, lamp 102 will not be energized and battery 120 may be charged if plug 118 is operated by an alternating current source.

One of the advantages of the present invention is a wheeled cart suitable for drying and sterilizing mop cords.

Another advantage of the present invention is a cart-carried compartment suitable for wringing out the cordlike ends of a mop.

Still another advantage of the present invention is a cord sterilizing compartment carried by a cart.

Yet another advantage of the present invention is an ultraviolet radiating source which has the rays emanating therefrom reflectively directed from the walls of the compartment carrying the ultraviolet source.

A further advantage of the present invention is a mop-supporting bracket, adapted to maintain a mop handle in a vertical direction when its cord end is disposed for irradiation by ultraviolet means.

Another advantage of the present invention is a coverable opening of the ultraviolet contained compartment so as to insure the ultraviolet rays do not emerge outwardly therefrom.

Still another advantage of the present invention is drains for each of the aforementioned compartments insuring that such compartments may be effectively cleaned and emptied of accumulated moisture therein.

Yet another advantage of the present invention is a rechargeable battery source for use operating the aforementioned ultraviolet light generator, during periods in which the cart is being transported from place to place.

A further advantage of the present invention is an ultraviolet energizing apparatus which maintains such apparatus energized, selectively as desired, at times when the cart is in use at a temporary location and when the cart is stored at a fixed location for extended periods of time.

Thus, there is disclosed in the above description and in the drawings, an embodiment of the invention which fully and effectively accomplishes the objects thereof. However, it will become apparent to those skilled in the art, how to make variations and modifications to the instant invention. Therefore, this invention is to be limited, not by the specific disclosure herein, but only by the appending claims.

The embodiment of the invention in which an exclusive privilege or property is claimed are defined as follows:

I claim:

1. A mop sterilizer and dryer comprising a wheeled cart, said cart having a first compartment and a second compartment disposed in side-by-side relationship bounded by upstanding walls and defining at the top thereof a first open-mouth portion and a second open-mouth portion of said first compartment and said second compartment, respectively, a first removable cover and a second removable cover, said first cover and said second cover partially covering said first open-mouth portion and said second open-mouth portion respectively, a pair of wringer rollers, said pair of rollers being disposed in spaced-apart parallel relationship and journaled to said first cover, a crank handle, said crank handle carried by one of said pair of rollers, a removable liner underlying the rollers, said removable liner configured to and residing within said first compartment, means to drain said first compartment and said liner, at least one opening in said second cover, an ultraviolet generating lamp, said ultraviolet generating lamp being disposed and carried within said second compartment, said second compartment and a lowermost surface of said second cover being covered with an ultraviolet light ray reflecting medium, means to energize said lamp, means to maintain the handle of a cord type mop in a vertical direction over said at least one opening in said second cover whereby the cord end of said mop may be disposed through said at least one opening in said second cover and within said second compartment.

2. The apparatus as claimed in claim 1 wherein said means to drain said first compartment comprises a valve, said valve communicating with the interior of said liner and located adjacent the bottom of said first compartment.

3. The apparatus as claimed in claim 1 wherein said means to energize said lamp comprises a battery, an operating switch, said lamp and said battery and said operating switch being disposed in a first series electrical circuit, a line cord, a rectifier, said line cord being disposed in a second series electrical circuit with said rectifier and said battery, wherein said battery is chargeable upon applying alternating current to said line cord.

4. The apparatus as claimed in claim 1 wherein said means to maintain comprises a bracket, one end of said bracket fixedly secured to said second cover, said bracket extending upwardly over said second cover, the other end of said bracket terminating above said at least one opening in said second cover, a notch, said notch being located in said other end of said bracket, said notch being configured to provide lateral support to said handle when positioned therewithin.

5. The apparatus as claimed in claim 1 further comprising a lid, said lid pivotably secured to an uppermost lateral surface of said second cover, whereby said lid covers said at least one opening in said second cover when said lid is pivoted upwardly from a resting position when residing on said uppermost lateral surface of said second cover.

6. The apparatus as claimed in claim 1 further comprising a waterproof housing, said lamp being disposed in said waterproof housing, said waterproof housing being carried within said second compartment.

7. The apparatus as claimed in claim 1 further comprising a rod handle, said handle fixedly secured to said cart and outstanding therefrom, said handle being disposed residing in a horizontal plane.

8. The apparatus as claimed in claim 1 further comprising a drain opening being disposed in said second compartment, a drain plug, said drain plug being removably disposed within said drain opening.

9. The apparatus as claimed in claim 1 further comprising means to rotationally couple said pair of rollers together.

* * * * *